(12) United States Patent
Lee et al.

(10) Patent No.: US 12,329,796 B2
(45) Date of Patent: Jun. 17, 2025

(54) ANTI-OBESITY COMPOSITION (71) Applicant: NATURAL ENDOTECH CO., LTD., Gyeonggi-do (KR)

(72) Inventors: Yong Wook Lee, Gyeonggi-do (KR); Chan Sung Park, Seoul (KR); Joo Hyun Oh, Gyeonggi-do (KR); Ji Min Kim, Gyeonggi-do (KR); Ha Neul Jo, Gyeonggi-do (KR)

(73) Assignee: NATURAL ENDOTECH CO., LTD., Gyeonggi-do (KR)

( * ) Notice: Subject to any disclaimer, the term of this patent is extended or adjusted under 35 U.S.C. 154(b) by 284 days.

(21) Appl. No.: 18/008,219

(22) PCT Filed: May 24, 2021

(86) PCT No.: PCT/KR2021/006436
§ 371 (c)(1),
(2) Date: Dec. 5, 2022

(87) PCT Pub. No.: WO2021/246703
PCT Pub. Date: Dec. 9, 2021

(65) Prior Publication Data
US 2023/0201289 A1    Jun. 29, 2023

(30) Foreign Application Priority Data

Jun. 5, 2020 (KR) .................. 10-2020-0068218

(51) Int. Cl.
*A61K 36/27* (2006.01)
*A61K 9/00* (2006.01)
*A61K 36/232* (2006.01)
*A61K 36/53* (2006.01)
*A61P 3/04* (2006.01)

(52) U.S. Cl.
CPC ............ *A61K 36/27* (2013.01); *A61K 9/0056* (2013.01); *A61K 36/232* (2013.01); *A61K 36/53* (2013.01); *A61P 3/04* (2018.01); *A61K 2236/333* (2013.01)

(58) Field of Classification Search
None
See application file for complete search history.

(56) References Cited

FOREIGN PATENT DOCUMENTS

| | | |
|---|---|---|
| KR | 10-1999-0011833 A | 2/1999 |
| KR | 10-2005-0111658 A | 11/2005 |
| KR | 10-1157214 B1 | 6/2012 |
| KR | 10-1969236 B1 | 7/2019 |
| KR | 10-2019-0106587 A | 9/2019 |

OTHER PUBLICATIONS

Sang (KR 20160131656 A—English translation)—2016.*
Choi (KR 20190106587—English translation)—Sep. 18, 2019.*
International Search Report from corresponding PCT Application No. PCT/KR2021/006436, dated Sep. 9, 2021.

* cited by examiner

*Primary Examiner* — Susan Hoffman
(74) *Attorney, Agent, or Firm* — Harness, Dickey & Pierce, P.L.C.

(57) ABSTRACT

The present invention relates to a composition for prevention, alleviation, or treatment of obesity.

3 Claims, 4 Drawing Sheets

ANTI-OBESITY COMPOSITION

CROSS-REFERENCE TO RELATED APPLICATIONS

This application is a national phase application of PCT Application No. PCT/KR2021/006436, filed on May 24, 2021, which claims the benefit and priority to Korean Patent Application No. 10-2020-0068218, filed on Jun. 5, 2020. The entire disclosures of the applications identified in this paragraph are incorporated herein by references.

TECHNICAL FIELD

The present disclosure relates to a composition for prevention, alleviation, or treatment of obesity.

BACKGROUND ART

In the dietary culture of contemporary people, the intake of simple sugars, meat, and fat is rapidly increasing due to the overflow of instant foods and the westernization of dietary life in line with the trend of pursuing convenience and improvement of living environment. In addition, stress from a busy social life, lack of exercise, and excessive intake of food act as causes of increasing obesity patients. As a result, the prevalence of various chronic adult diseases is increasing, and these diseases have been observed to have very close relationship with obesity as analyzed by epidemiological studies. Moreover, a proposal of innovative methods for alleviating or treating obesity is required for the prevention and treatment of adult diseases, the seriousness of which has recently emerged socially and economically.

Obesity is a phenomenon in which excess energy is accumulated as body fat due to an imbalance between energy obtained through food intake and energy consumed through physical activity. In general, obesity refers to a condition in which there is an excess of adipose tissues in the body. Persistence of such obese conditions over a long period of time induces various metabolic diseases and adult diseases such as diabetes, hyperlipidemia, heart disease, stroke, arteriosclerosis, and fatty liver. Excessive energy supply increases the size and number of fat cells which are then stored as fat in the body, acting as a main cause of obesity. It is also known that obesity is induced by various causes such as genetic factors, environmental factors attributed to westernized dietary habits, psychological factors, and abnormal energy metabolism.

Obesity, which is a type of metabolic disease caused by an imbalance between calorie intake and consumption, refers to a condition in which much more fat is accumulated in the body than the amount of fat necessary for the function of adipose tissues, provoking a disorder in normal biochemical and physiological functions in the human body. Obesity not only gives rise to inconvenience in physical activity, reduced work efficiency, and abnormal growth of body, but also acts as a cause of various diseases such as diabetes, hyperlipidemia, elevated blood cholesterol, kidney disease, stroke, fatty liver, coronary artery disease, and joint disease. As the incidence of obesity has increased rapidly over the past several decades, interest in obesity continues to rise, and it is recognized that the cause of obesity is determined by a combination of environmental factors and environmental factors that destroy energy balance, rather than simply genetic causes.

In the body, adipocytes function as cells that accumulate energy necessary for the body. In this regard, adipocytes decompose triglycerides as needed. Adipose tissues are known to play a role as an endocrine in regulating energy metabolism in the body, including fat metabolism and sugar metabolism, as well as functioning to accumulate energy. Adipocytes are differentiated from mesenchymal precursors through preadipocytes. During the differentiation process, adipocytes are accumulated as fats in the body through morphological and biochemical changes, and adipose tissues increase in size and are differentiated from new adipocytes. The size of these adipocytes is possible to regulate by dietary control, but the process of differentiating new preadipocytes into adipocytes is not effective with dietary control. Thus, in order to fundamentally treat or suppress obesity, it is important to regulate the differentiation process of adipocytes.

The tasks of treating obesity can be divided into two main categories: the one task is to lose weight by burning excess fats and the other is designed to alleviate metabolic imbalance. Current treatment of obesity aims not only to lose weight, but also to alleviate metabolic abnormalities by removing factors that cause cardiovascular disease at an early stage. In addition, active studies have been conducted into suppressing obesity through control of dietary intake and energy consumption.

Anti-obesity drugs known to date are largely divided into satiety enhancers, fat absorption inhibitors, and antipsychotic appetite suppressants according to their mechanism of action. Representative of anti-obesity drugs are Xenical (Roche Pharmaceuticals, Switzerland), Reductil (Abbott, USA), and Exolise (Atopharma, France). However, these drugs suffer from the disadvantages of causing steatorrhea, intestinal gas generation, abdominal distension, defecation incontinence, etc., provoking adverse effects such as heart disease, respiratory disease, and nervous system disease, and being short in efficacy duration.

Therefore, there is an urgent need for developing functional materials effective for weight control from natural materials in order to minimize the side effects of artificially synthesized materials as described in the foregoing.

DETAILED DESCRIPTION

Technical Problem

Accordingly, the present inventors have tried to find a natural product that is excellent for obesity suppression, and as a result, through tissue analysis through animal model experiments, a composition effective for preventing, alleviating, or treating obesity.

An aspect of the present disclosure is to provide a food composition for prevention or alleviation of obesity.

Another aspect of the present disclosure is to a pharmaceutical composition for prevention or treatment of obesity.

Technical Solution

The present disclosure pertains to a composition for prevention, alleviation, or treatment of obesity.

Below, a detailed description will be given of the present disclosure.

An aspect of the present disclosure is drawn to a food composition including an extract from at least one selected from the group consisting of *Cynanchi Wilfordii* Radix, *Phlomis umbrosa* TURCZ. and an *Angelica* sp. for prevention or treatment of obesity.

In the present disclosure, the obesity may be diet-induced obesity, neurogenic obesity, gastritis obesity, gluten obesity, obesity due to venous circulation disorder, or metabolic obesity, but is not limited thereto.

In the present invention, the metabolic obesity may be a cause of diabetes, hyperlipidemia, heart disease, stroke, atherosclerosis, or fatty liver, but with no limitations thereto.

*Cynanchi Wilfordii* Radix originates from the plant *Cynanchum wilfordii* Hemsley, which is a vine plant growing in sunny meadows at the foot of mountains or on costal slopes. The roots of the plant are harvested from fall to winter, dried, and then used as a medicine. *Cynanchi Wilfordii* Radix is sweet and slightly bitter in taste and has a slightly warm property. In the sense of oriental medicine, this medicine replenishes the energy of the liver and kidneys, strengthens muscles and bones, improves digestion, and has the function of detoxification. Taking advantage of these effects, *Cynanchi Wilfordii* Radix is applied to the treatment of liver and kidney deficiency syndrome, impotence syndrome, nocturnal emission, soreness of the waist and knees, spleen deficiency, abdominal fullness, diarrhea, early gray hairs compared to age, and insufficient milk secretion after childbirth.

*Phlomis umbrosa* TURCZ., which is a perennial herb belonging to the Lamiaceae family, is used as an alternative to the dried root of *Dipsacus japonicus* Miq. Due to the rarity thereof. The Chinese name of *Phlomis umbrosa* TURCZ. was given because it treats fractures well. Its components include alkaloids, essential oils, vitamin E, etc. The plant is mild in medicinal property and bitter in taste. This medicinal material is effective for the treatment of low back pain caused by hepatic or renal dysfunction and the poor skeletal and muscular movement of the legs. *Phlomis umbrosa* TURCZ. is also therapeutically effective for arthritis and rheumatoid arthritis and is often applied to the treatment of hernia of intervertebral discs and bruises in the back. For women, it can prevent miscarriage when administered during pregnancy, and has the effect of stopping bleeding even when menstruation is excessive or uterine bleeding is severe. For the elderly, it is often used for numbness and pain due to gait disorders due to lack of strength in the lower body or poor flexion and extension. *Phlomis umbrosa* TURCZ. is recommended to avoid simultaneous use with *Rehmannia glutinosa* var. *purpurea* and is not used for treating dysentery. A typical prescription formulation is a pill of *Phlomis umbrosa* TURCZ. Its gemmules are eaten as a vegetable food.

As used herein, the term "*Angelica*" refers to a dried root from *Angelica gigas* Nakai in Korea, *Angelica sinensis* (Oliv.) Diels in China, and *Angelica acutiloba* (Siebold. & Zucc.) Kitag. or *Angelica acutiloba* (Siebold. & Zucc.) Kitag. var. sugiyamae Hikino in Japanese. It is said that the Chinese character of *angelica* was given with the meaning of wanting to return. This name meaning originated from a custom long ago in China where wives worried about their husbands going to the battlefield and put *angelica* in their clothes because it was believed that when energy was exhausted in the battlefield, the intake of *angelica* would restore energy and thus the husbands could return back to their wives. According to one theory, it is also named after saying that if this medicine is taken, the vigorous energy will return to the original state. This medicine is warm in vigorous property and sweet and spicy in taste. In general, *Angelica gigas* Nakai is weaker in sweet taste and spicier than *Angelica sinensis* (Oliv.) Diels or *Angelica acutiloba* (Siebold. & Zucc.) Kitag. *Angelica*'s efficacy resorts mainly to blood supplementation, which aid to produce blood when blood is scarce. The roots from *Angelica sinensis* (Oliv.) Diels or *Angelica acutiloba* (Siebold. & Zucc.) Kitag are superb in blood supplementation. However, the roots from *Angelica gigas* Nakai are high in blood circulating activity rather than blood supplementation and exhibits strong anticancer and antihypertensive effects. Pharmaceutically, *angelica* promotes the blood flow in the coronary artery and accelerates red blood cells. *Angelica* is given various names in Korea, China, and Japan, such as to-dang-gwi, soong-geom-cho, or Jo-seon-dang-gwi in Korea, Dānggui, wengu-I, Qián guī, Dà qín, Xiàng mǎ, or de xiān yuan in China, and Ni~Tsu tōki in Japan.

In the present disclosure, the composition may include an extract from at least one selected from the group consisting of *Cynanchi Wilfordii* Radix, *Phlomis umbrosa* TURCZ., and *angelica*, for example, an extract from a mixture of *Cynanchi Wilfordii* Radix, *Phlomis umbrosa* TURCZ. and *angelica*, or a mixture of a *Cynanchi Wilfordii* Radix extract, a *Phlomis umbrosa* TURCZ. extract, and an *angelica* extract.

In the present disclosure, the *Cynanchi Wilfordii* Radix extract may be an extract prepared using at least one selected from roots, stems, and leaves of the *Cynanchi Wilfordii* Radix, for example, an extract from the roots, but with no limitations thereto.

In the present disclosure, the *Phlomis umbrosa* TURCZ. extract may be an extract prepared using at least one selected from roots, stems, and leaves of the *Phlomis umbrosa* TURCZ., for example, an extract from the roots, but with no limitations thereto.

In the present disclosure, the *angelica* extract may be an extract prepared using at least one selected from roots, stems, and leaves of the *Phlomis umbrosa* TURCZ., for example, an extract from the roots, but with no limitations thereto.

The extract of the present disclosure may be a crude extract obtained by extraction with at least one solvent selected from the group consisting of water and a straight or branched alcohol of 1 to 4 carbon atoms, for example, a crude extract prepared using water as a solvent.

When used as a solvent for preparing a crude extract of the present disclosure, a mixture of water and alcohol may be an aqueous solution containing a straight or branched alcohol of 1 to 4 carbon atoms in an amount of 10% to 100% (v/v) (exclusive), 20% to 100% (v/v) (exclusive), 30% to 100% (v/v) (exclusive), 40% to 100% (v/v) (exclusive), 50% to 100% (v/v) (exclusive), 60% to 100% (v/v) (exclusive), or 70% to 100% (v/v) (exclusive).

In the present disclosure, the aqueous alcohol solution may be at least one selected from the group consisting of an aqueous methanol solution, an aqueous ethanol solution, an aqueous propanol solution, and an aqueous butanol solution, but is not limited thereto.

The extract according to the present disclosure may be a solvent fraction obtained by fractionating the crude solvent extract with an additional solvent.

The content of the extract as an active ingredient in the composition according to the present disclosure may be appropriately adjusted depending on the type and purpose of use, the patient's condition, the type and severity of symptoms, etc. and may be, for example, 0.001 to 99.9% by weight or 0.1 to 99.9% by weight and preferably 0.1 to 50% by weight or 0.1 to 40% by weight, based on the weight of the solid content, with no limitations thereto.

Hereinafter, a process for preparation of the extract according to the present disclosure will be described in greater detail.

At least one selected from the group consisting of *Cynanchi Wilfordii* Radix, *Phlomis umbrosa* TURCZ. and *angelica* is sectioned, washed with water to remove foreign substances, dried, and then subjected to reflux extraction with an extraction solvent. In this regard, the extraction solvent may be used in an amount of 5- to 20-fold volumes of the weight of the at least one selected from the group consisting of *Cynanchi Wilfordii* Radix, *Phlomis umbrosa* TURCZ. and *angelica* and preferably in an amount of 7- to 15-fold volumes. The extraction was followed by filtration. The filtrate was collected. No particular limitations are imparted to the extraction temperature, but the extraction is conducted at a temperature of 40 to 110° C. and preferably at temperature of 55 to 105° C.

The extraction process may be performed once or many times. In a particular embodiment of the present disclosure, re-extraction may be performed after primary extraction. In the case of mass production of herb medicinal extracts, a loss occurs due to the high water content of the herb medicine itself even if effective filtration is conducted. Thus, only low extraction efficiency is obtained after primary extraction. The re-extraction is to prevent the low extraction efficiency. In addition, as a result of examining the extraction efficiency at each stage, it was found that the extract obtained until secondary extraction amounts to 80 to 90% of the total extract.

In the present disclosure, when the extraction process is repeated twice, the residue obtained after primary extraction is subjected to reflux extraction with about 5 to 15 volumes of an extraction solvent and preferably with 8 to 12 volumes of an extraction solvent. Following extraction, filtration was performed. The filtrate was pooled together with that obtained previously and the pool was concentrated in a vacuum to afford an extract as a concentrate.

Although the extraction efficiency can be increased by mixing the filtrates obtained after two rounds of extraction, the extract of the present disclosure is not limited by the number of extractions.

If too small an amount of the solvent is used in preparing the extract of the present disclosure, it is difficult to stir the solution and the solubility of the extract decreases, resulting in a decrease in extraction efficiency. When the solvent is used in an excessively large amount, the amount of solvent treated in the subsequent purification step increases, making it uneconomical and causing problems in handling. Hence, the solvent may be preferably used within the range.

In order to adjust the content of the remaining lower alcohol in the obtained concentrate so as to make it suitable for use as raw material for medicine, the concentrate may be subjected to 1 to 5 rounds and preferably 2 to 3 rounds of azeotropic concentration with about 10 to 30 times, preferably 15 to 25 times, more preferably about 20 times by weight of water, based on the total amount of the concentrate, and equivalent amount of water is added thereto to homogenously suspend the same. The suspension is then lyophilized and/or spray dried to prepare and extract in a powder form.

In the present disclosure, the composition may be administered to mammals including humans via various routes. All modes of administration that are usually used are contemplated. For example, administration may be performed through oral, transdermal, intravenous, intramuscular, subcutaneous, and other routes, with preference for an oral route.

In the present disclosure, the food composition may be a food, a beverage, a food additive, or the like.

The content of the extract as an active ingredient contained in the food composition may appropriately vary depending on the form of food, desired use, etc., with no specific limitations thereto. For example, it may be added in an amount of 0.01 to 15 wt % of the total food, and for health beverage composition, it can be added in an amount of 0.02 to 10 g, preferably 0.3 to 1 g, based on 100 ml of the composition.

Provided that the beverage composition of the present disclosure contains the above-described extract as an essential component at the indicated ratio, no particular limitations are imparted to the other liquid components, wherein the other components may include various flavorants or natural carbohydrates as in conventional beverage.

Examples of the natural carbohydrates include typical sugars, such as monosaccharides, e.g., glucose, fructose, etc., disaccharides, e.g., maltose, sucrose, etc., and polysaccharides, e.g., dextrin, cyclodextrin, etc., and sugar alcohols such as xylitol, sorbitol, erythritol, etc.

In addition to those described above, natural flavorants (taumatin, *stevia* extract (e.g., levaudioside A, glycyrrhizin, and the like), and synthetic flavorants (saccharin, aspartame, and the like) may be advantageously used. The amount of the natural carbohydrate generally ranges from about 1 to 20 g and preferably from about 5 to 12 g per 100 ml of the composition of the present disclosure.

The composition of the present disclosure may contain are various nutrients, vitamins, minerals (electrolytes), aromatics such as synthetic and natural aromatics, colorants, thickeners, (cheese, chocolate, etc.), pectic acid and a salt thereof, alginic add and a salt thereof, organic acid, protective colloidal thickeners, pH adjusting agents, stabilizers, preservatives, glycerin, alcohols, carbonizing agents used in carbonate beverage, and etc. These ingredients may be used independently or in combination. Further, the composition of the present disclosure may contain fruit flesh for use in preparing natural fruit juice, fruit juice beverages, and vegetable beverages. The ratio of the additives is not so important, but may be generally in the range of about 0 to 20 parts by weight based on 100 parts by weight of the present disclosure.

In particular, when the extract of the present disclosure is administered to the human body, it is considered that there is no concern about side effects compared to other synthetic drugs in view of the general characteristics of natural extracts. In fact, as a result of the toxicity test on the standardized herbal composition, the extract was found to have no toxic effects on the living body.

Another aspect of the present disclosure is drawn to a pharmaceutical composition comprising an extract from at least one selected from the group consisting of *Cynanchi Wilfordii* Radix, *Phlomis umbrosa* TURCZ. and *angelica* for prevention or treatment of obesity.

In the present disclosure, the obesity may be diet-induced obesity, neurogenic obesity, gastritis obesity, gluten obesity, obesity due to venous circulation disorder, or metabolic obesity, but is not limited thereto.

In the present invention, the metabolic obesity may be a cause of diabetes, hyperlipidemia, heart disease, stroke, atherosclerosis, or fatty liver, but with no limitations thereto.

In the present disclosure, the extract of the present disclosure may be a crude extract obtained by extraction with at least one solvent selected from the group consisting of water and a straight or branched alcohol of 1 to 4 carbon atoms, for example, a crude extract prepared using water as a solvent.

The extract is the same as that described above, so its description is omitted.

In the present disclosure, the composition may be administered to mammals including humans via various routes. All modes of administration that are usually used are contemplated. For example, administration may be performed through oral, transdermal, intravenous, intramuscular, subcutaneous, and other routes, with preference for an oral route.

In the present disclosure, the composition may be formulated into oral dosage forms such as pulvis, granules, tablets, capsules, ointments, suspensions, emulsions, syrups, aerosols, and the like or parenteral dosage forms such as transdermal agents, suppositories, and sterile injections.

In the present disclosure, the pharmaceutical composition may further include pharmaceutically suitable and physiologically acceptable auxiliary agents such as a carrier, an excipient, and a diluent in addition to the mixed extract.

In the present disclosure, the carrier, excipient, and diluent which may be contained in the composition may exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

When the composition is formulated, diluents or excipients such as fillers, extenders, binders, wetting agents, disintegrants, surfactants, etc. may be used. A solid formulation for oral administration may include a tablet, a pill, a powder, granules, a capsule, etc. Such solid formulations may be prepared by mixing the strain or the vesicle derived from the strain with at least one excipient, for example, starch, calcium carbonate, sucrose or lactose, gelatin, etc. In addition to the simple excipients, a lubricant, such as magnesium stearate or talc, may be used.

A liquid formulation for oral administration may include a suspension, a solution for internal use, an emulsion, a syrup, etc. In addition to a simple diluent commonly used, such as water and liquid paraffin, the formulation may include various excipients such as a humectant, a sweetener, an aromatic, a preservative, etc.

A formulation for parenteral administration may include a sterilized aqueous solution, a non-aqueous solvent, a suspension, an emulsion, a lyophilized formulation, a suppository, a transdermal agent, etc. The non-aqueous solvent and the suspension may include propylene glycol, polyethylene glycol, a vegetable oil such as olive oil, an injectable ester such as ethyl oleate, etc.

As a base of the suppository, witepsol, macrogol, Tween 61, cocoa butter, laurin butter, glycerogelatin, etc. may be used.

In an embodiment of applying the composition of the present disclosure to humans, the composition of the present disclosure may be administered alone, but generally in combination with a pharmaceutical carrier selected in consideration of administration modes and standard pharmaceutical practice.

By way of example, the pharmaceutical composition may be administered orally, intraorally, or sublingually in the form of a tablet containing starch or lactose, a capsule containing a suitable excipient, or an elixir or suspension containing a flavoring or coloring agent. Such liquid agents may be formulated together with a pharmaceutically acceptable additive such as a suspending agent (e.g., semi-synthetic glycerides such as methyl cellulose and Witepsol, a mixture of apricot kernel oil and PEG-6 ester, or a glyceride mixture of PEG-8 and caprylic/capric glyceride).

The dose of the composition of the present invention may vary depending on patient's age, weight, and sex, a mode of administration, patients' health conditions, and the severity of disease, and it may be administered once to several times as divided a day at certain intervals according to the judgment of doctors or pharmacists. For example, the daily dose may range from 0.1 to 500 mg/kg and preferably from 0.5 to 300 mg/kg on the basis of content of the active ingredient. The dosage is an example of average cases and the dosage may be higher or lower according to the difference of individuals.

When the daily dosage of the composition of the present disclosure is below the lower limit of the dose range, a significant effect cannot be obtained. A dose higher than the upper limit is economically disadvantageous. It is recommended to use the composition within the aforementioned range because an amount deviating a usual dose range may be apt to cause undesired side effects.

So long as it is usually available, any extraction method may be applied to the present disclosure. Examples of the extraction method include cold precipitation, hot water extraction, ultrasonic extraction, and reflux cold precipitation, with preference for hot water extraction, but are not limited thereto.

Advantageous Effects

The present disclosure relates to a composition for prevention, alleviation, or treatment of obesity. The composition according to the present disclosure may be available as a composition useful for preventing, alleviating, or treating obesity.

BEST MODE FOR CARRYING OUT THE INVENTION

The present disclosure relates to a food composition including an extract from at least one selected from the group consisting of *Cynanchi Wilfordii* Radix, *Phlomis umbrosa* TURCZ., and *angelica* for prevention or alleviation of obesity.

Mode for Carrying Out the Invention

A better understanding of the present disclosure may be obtained through the following examples which are set forth to illustrate, but are not to be construed as limiting the present disclosure.

Example 1. Preparation of Crude Extract

The natural herbal materials *Cynanchum wilfordii* roots, *Phlomis umbrosa* roots, and *Angelica gigas* roots were mixed at a weight ratio of 1:1:1.08 and subjected to extraction by heating in 10 volumes of water at 95 to 105° C. for 8 hours. Following filtration, the filtrate thus obtained was lyophilized at −80° C. to afford a crude extract as a powder.

Experimental Example 1. Evaluation for Effect of Extract on Obesity-Induced Mice 1-1. Preparation of Experimental Animal and Raising Condition C57BL/J male mice, 5 weeks old, were purchased from Samtako Bio Korea and then acclimated to a raising room (temperature: 22±2° C., humidity: 50±5%, light condition: 12-hour light/dark cycle) for one week before use in experiments.

A normal group was fed with AIN-93G (Nor; Diet D10012G, Research Diets, Inc., New Brunswick, N.J., USA) while a high-fat diet group was supplied with 60% high-fat diet (HFD) purchased from Diet (Diet 12492, Research Diets, Inc., New Brunswick, N.J., USA).

1-2. Administration of High-Fat Diet and Test Material to Mice

C57BL/J male mice were divided into five groups of 10 according to a randomized block design (mixed model of random and fixed factors).

As shown in Table 1, below, the normal diet was fed to a normal group, HFD to a control group, and HFD in combination with 100, 200, and 400 mg/kg of the extract prepared in the Example to respective test groups.

TABLE 1

| Group | Inducing condition | Test material | Dose | Sex | No. of animals |
|---|---|---|---|---|---|
| Normal | Normal diet (AIN-93G) | Physiological saline | 0 | Male | 10 |
| Control | High fat diet | Physiological saline | 0 | Male | 10 |
| Example 100 | | Example 100 mg/kg | 100 | Male | 10 |
| Example 200 | | Example 200 mg/kg | 200 | Male | 10 |
| Example 400 | | Example 400 mg/kg | 400 | Male | 10 |

To the normal and control groups, which were fed with the normal diet and HFD, respectively, but not with the test materials, physiological saline was orally administered at the same dose (0.2 ml/mouse/day).

One day before completion of the experiment, 60 mice in the six groups were fasted for 12 hours. On the last day of the experiment, the mice were anesthetized, and blood was collected from the orbit. Plasma was separated from the collected blood and stored in a freezer at −80° C. Adipose tissues and organs were excised from the mice and weighed.

1-3. Weight Change, Food Intake, and Food Efficiency Ratio in Mice

While the extract of the Example was orally administered for eight weeks, the mice were monitored for weight change and food intake at a predetermined point of time every week. Examination was made of total weight gain and average daily weight gain (total body weight gain/days. After food intake (total food intake/days) was measured, the food efficiency ratio was calculated as follows. The results are summarized in Table 2, below.

Food Efficiency Ratio=Total weight gain/Total food intake×100  [Equation 1]

TABLE 2

| Group | Inducing condition | Weight gain (g) | Food intake (g/day) | Food efficiency ratio (body weight gain/food intake) |
|---|---|---|---|---|
| Normal | Normal diet (AIN-93G) | 4.50 ± 1.28 *** | 2.44 ± 0.19 | 1.01 ± 0.48 |
| Control | High fat diet | 12.66 ± 2.26 | 1.92 ± 0.51 | 3.88 ± 2.04 |
| Example 100 | | 9.38 ± 2.55* | 1.73 ± 0.47 | 3.68 ± 1.82 |
| Example 200 | | 9.55 ± 2.64* | 1.82 ± 0.47 | 3.69 ± 1.76 |
| Example 400 | | 10.87 ± 3.17 | 1.91 ± 0.45 | 3.80 ± 1.80 |

Comparative control with statistical significance *: p<0.05

The extract of the Example was assayed for anti-obesity effect on HFD-fed mice. A significant weight gain was observed in the HFD-fed control which weighed 12.66±2.26 g, compared to the normal group weighing 4.50±1.28 g (P<0.001).

The extract of the Example exhibited a weight gain of 9.38±2.55 at a dose of 100 mg/kg (P<0.05) and 9.55±2.64 at a dose of 200 mg/kg (P<0.05), with statistical significance.

The food intake was reduced in the HFD-fed high-fat diet groups, compared to the normal diet-fed normal group. However, no significant differences in food intake were observed among the HFD-fed groups.

Experimental Example 2. Serobiochemical Assay

The blood obtained after completion of the experiment was centrifuged at 3,000 rpm for 20 minutes to separate serum for use in analyzing biochemical indices.

Figure 1A:
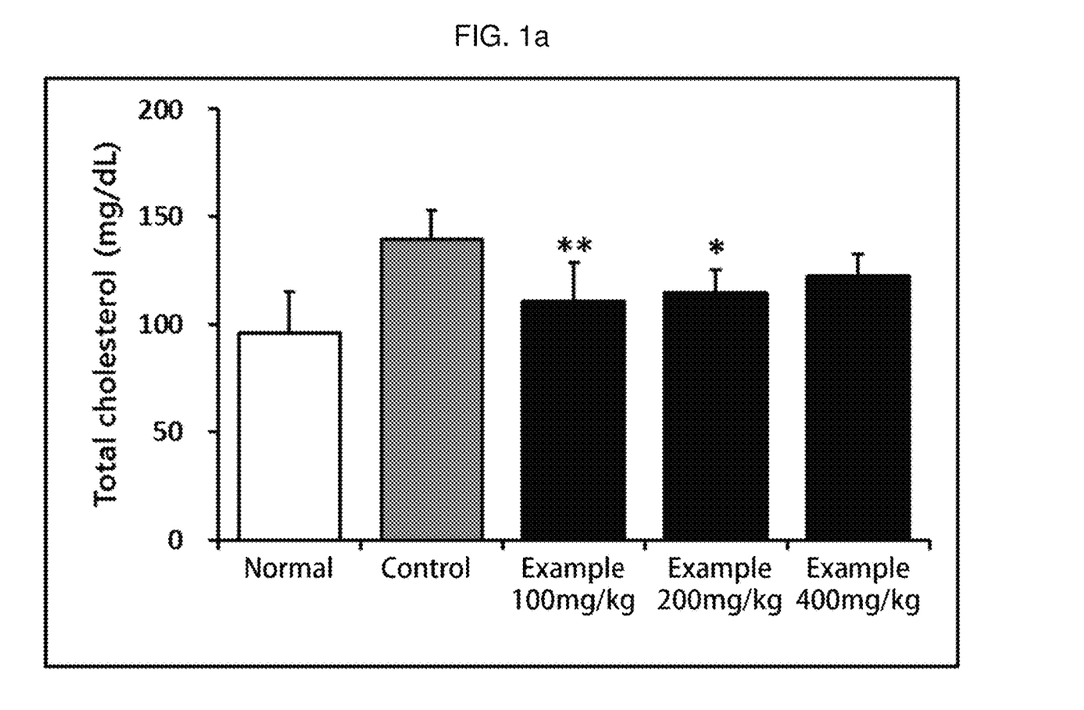
FIG. 1a is a graph of blood total cholesterol levels as measured according to an embodiment of the present disclosure.
Figure 1B:
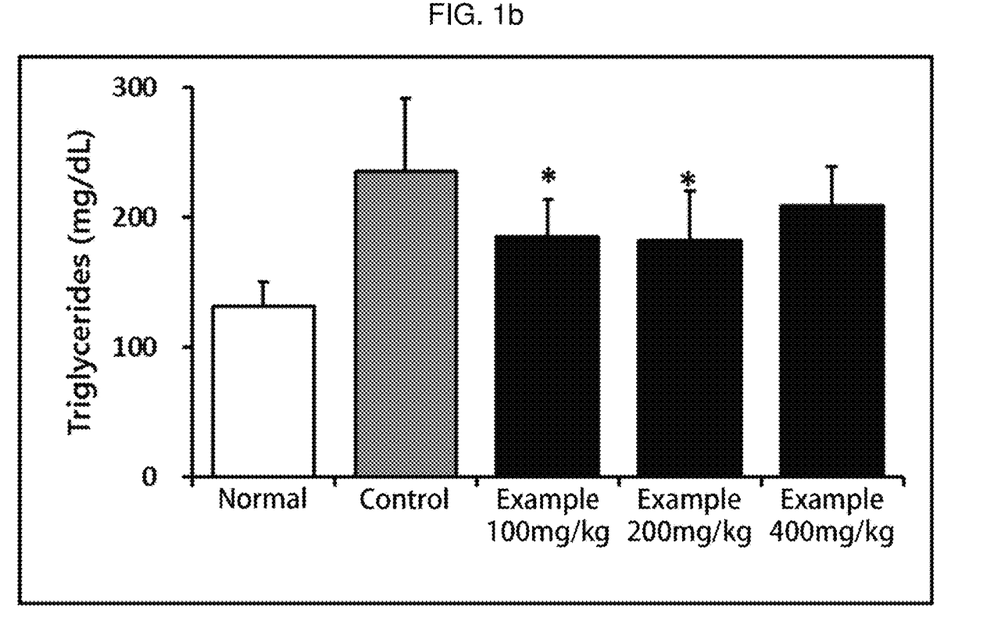
FIG. 1b is a graph of blood total triglyceride levels as measured according to an embodiment of the present disclosure.

The separated serum was measured for lipid contents in terms of total cholesterol and triglyceride, and the measurements are summarized in Table 3 and depicted in FIGS. 1a and 1b.

TABLE 3

| Group | Inducing condition | Total cholesterol (mg/dL) | Triglyceride (mg/dL) |
|---|---|---|---|
| Normal | Normal diet (AIN-93G) | 96.17 ± 2.75 *** | 132.30 ± 2.63 *** |
| Control | High fat diet | 139.08 ± 1.99 | 235.76 ± 7.96 |
| Example 100 | | 110.72 ± 2.57 ** | 185.09 ± 4.22 * |
| Example 200 | | 114.63 ± 1.48 * | 182.32 ± 5.53 * |
| Example 400 | | 122.43 ± 1.44 | 209.83 ± 4.23 |

Comparative control with statistical significance *: p<0.05, **: p<0.01

The blood total cholesterol level in each group was measured to be 96.17 mg/dL in the normal group and 139.1 mg/dL in the control, indicating that HFD increases the total cholesterol level.

When the extract of the Example was fed, the total cholesterol level was measured to be 110.7 mg/dL at a dose of 100 mg/kg, 114.6 mg/dL at a dose of 200 mg/kg, and 122.43 mg/dL at a dose of 400 mg/kg.

In particular, the groups fed with the extract of the Example at a dose of 100 mg/kg and 200 mg/kg decreased in total cholesterol level, with significance.

The blood triglyceride level in each group was measured to be 132.3 mg/dL in the normal group and 235.8 mg/dL in the control, indicating that HFD increases the blood triglyceride level.

When the extract of the Example was fed, the blood triglyceride level was measured to be 185.1 mg/dL at a dose of 100 mg/kg, 182.3 mg/dL at a dose of 200 mg/kg, and 209.8 mg/dL at a dose of 400 mg/kg.

From the data, it was understood that the groups fed with the extract of the Example at a dose of 100 mg/kg and 200 mg/kg decreased in blood triglyceride level, with significance.

Experimental Example 3. Fat Content in Mouse Adipose Tissue

Figure 2A:
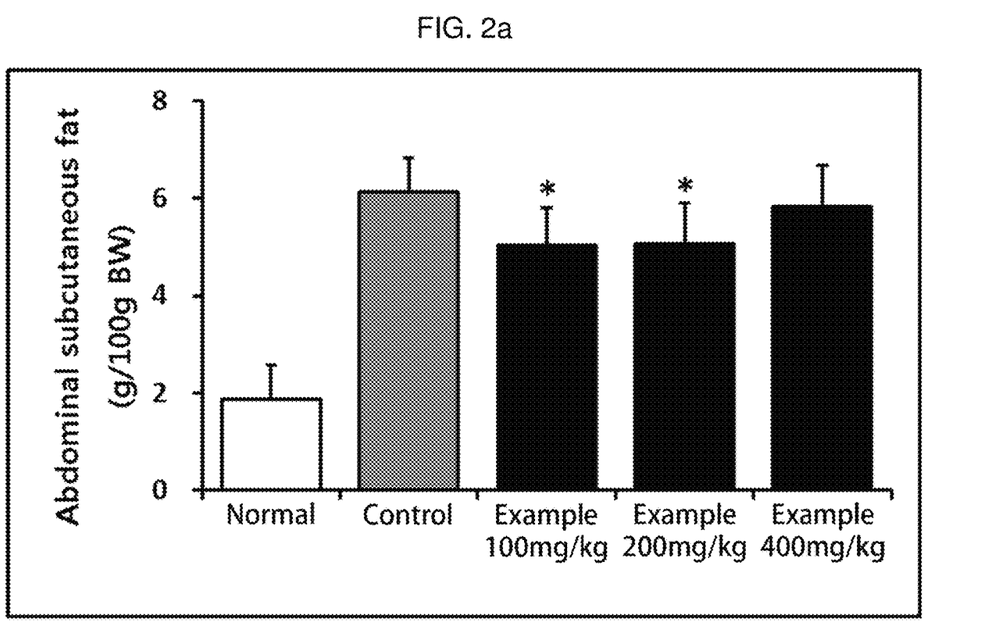
FIG. 2a is a graph of abdominal subcutaneous fat levels as measured according to an embodiment of the present disclosure.
Figure 2B:
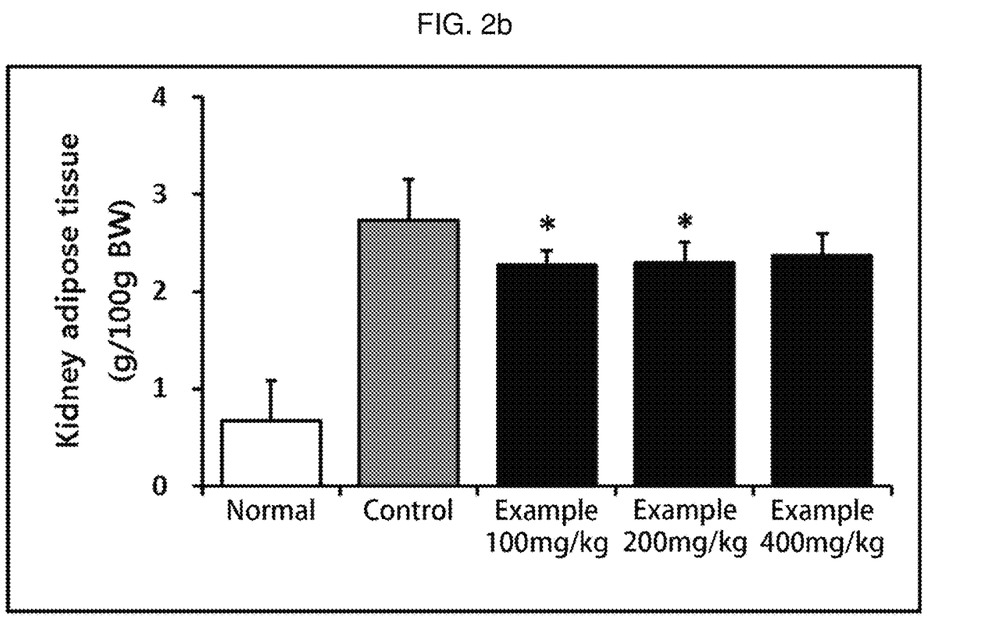
FIG. 2b is a graph of peri-renal fat levels as measured according to an embodiment of the present disclosure.

To examine the effect of the extract of the Example on adipose tissues, peri-abdominal and peri-renal total fats were weighed. The anti-obesity effect on the adipose tissues was analyzed by measuring abdominal subcutaneous fat and the measurements are summarized in Table 4 and depicted in FIG. 2a. In addition, peri-renal total fat was weighed. The data are also summarized in Table 4 and depicted in FIG. 2b.

TABLE 4

| Group | Inducing condition | Peri-abdominal fat (g/100 g BW) | Peri-renal fat (g/100 g BW) |
| --- | --- | --- | --- |
| Normal | Normal diet (AIN-93G) | 1.89 ± 0.08 *** | 0.68 ± 0.05 *** |
| Control | High fat diet | 6.13 ± 0.10 | 2.73 ± 0.06 |
| Example 100 | | 5.04 ± 0.10 * | 2.27 ± 0.02 * |
| Example 200 | | 5.06 ± 0.11 * | 2.29 ± 0.03 * |
| Example 400 | | 5.83 ± 0.11 | 2.37 ± 0.03 |

Comparative control with statistical significance *: p<0.05

The peri-abdominal fat in each group was measured to be 6.13±0.10 (g/100 g BW) in the HFD-fed group which was about 2.13- to 5.67-fold higher than 1.89±0.08 (g/100 g BW) measured for the normal group.

When the extract of the Example was fed, the peri-abdominal fat was measured to be 5.04±0.10 (g/100 g BW) at a dose of 100 mg/kg, 5.06±0.11 (g/100 g BW) at a dose of 200 mg/kg, and 5.83±0.11 (g/100 g BW) at a dose of 400 mg/kg.

From the data, it was understood that the groups fed with the extract of the Example at a dose of 100 mg/kg and 200 mg/kg decreased in peri-abdominal fat level, with significance.

In addition, the peri-renal fat in each group was measured to be 2.73±0.06 (g/100 g BW) in the HFD-fed group which was higher than 0.68±0.05 (g/100 g BW) measured for the normal group.

When the extract of the Example was fed, the peri-abdominal fat was measured to be 2.27±0.02 (g/100 g BW) at a dose of 100 mg/kg, 2.29±0.03 (g/100 g BW) at a dose of 200 mg/kg, and 2.37±0.03 (g/100 g BW) at a dose of 400 mg/kg.

From the data, it was understood that the groups fed with the extract of the Example at a dose of 100 mg/kg and 200 mg/kg decreased in peri-renal fat level, with significance.

Experimental Example 4. Assay for Expression of Triglyceride Synthesis-Related Protein The extract of the Example was assayed for effect on the expression of triglyceride synthesis-related proteins in animal models of HFD-induced obesity. Adipose tissues were taken and subjected to Western blotting to measure expression levels of the obesity-related genes PPARr and GLUT4. As an internal control, the housekeeping gene actin, which is expressed in most types of cells, was also measured for expression level to normalize the protein expression. Expression results of the triglyceride synthesis-related proteins are depicted in FIG. 3.

Figure 3:
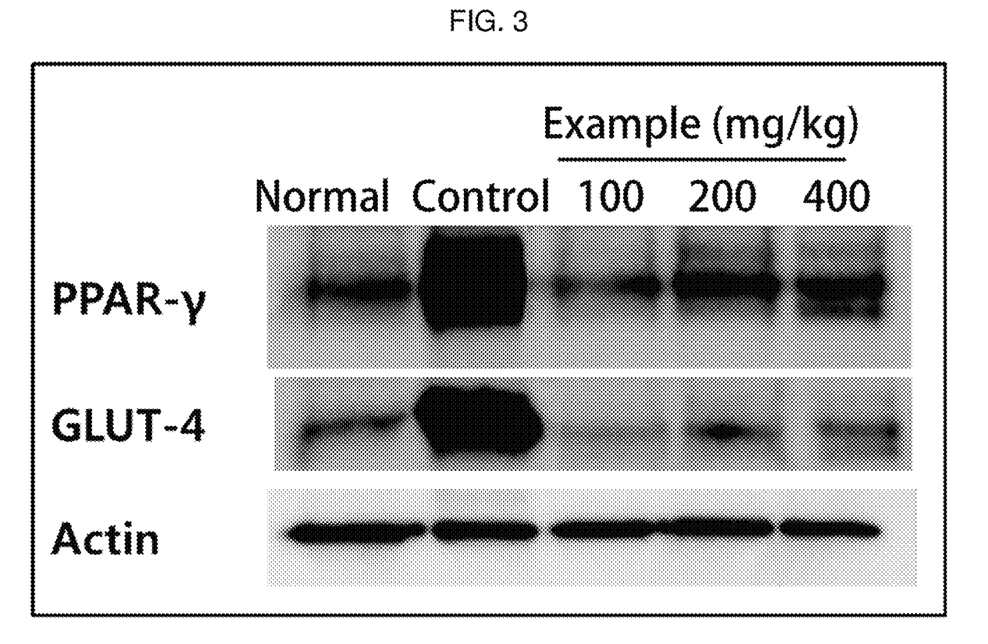
FIG. 3 is a photographic image of expression levels of triglyceride synthesis-related proteins as measured according to an embodiment of the present disclosure.

As can be seen in FIG. 3, the expression levels of the triglyceride synthesis-related proteins were greatly increased in the HFD-fed control, compared to the normal group. However, the administration of the extract of the Example reduced the expression levels of the triglyceride synthesis-related proteins.

Inter alia, the groups fed with 100 mg/kg and 200 mg/kg of the extract of the Example exhibited similar expression levels to that in the normal group, with significance on the anti-obesity effect.

The data demonstrate that the extract of the Example is effective for alleviating metabolic diseases.

INDUSTRIAL APPLICABILITY

The present disclosure relates to a composition for prevention, alleviation, or treatment of obesity.

What is claimed is:

1. A method for prevention, treatment or alleviation of obesity comprising:
administering, to a subject, a composition comprising an initial crude extract obtained by extraction with a solvent consisting of water from a combination consisting of Cynanchi Wilfordii Radix, Phlomis umbrosa TURCZ, and *angelica*,
wherein the extract reduces blood triglyceride levels and regulates expression of PPARγ and GLUT4 proteins.

2. The method of claim 1, wherein the obesity is diet-induced obesity, neurogenic obesity, gastritis obesity, gluten obesity, obesity due to venous circulation disorder, or obesity associated with metabolic syndrome.

3. The method of claim 2, wherein the obesity associated with metabolic syndrome is a cause of diabetes, hyperlipidemia, heart disease, stroke, atherosclerosis, or fatty liver.

* * * * *